(12) United States Patent
Dawber et al.

(10) Patent No.: US 6,320,886 B1
(45) Date of Patent: Nov. 20, 2001

(54) LASER DEVICE

(75) Inventors: William Dawber, Fareham; Jian Wang, St. Andrews; Malcolm H Dunn, St. Andrews; Cameron F Rae, St. Andrews, all of (GB)

(73) Assignee: The Secretary of Defence in Her Britannic Majesty's Government of the United Kingdom of Great Britian and Northern Ireland, Farnborough (GB)

( * ) Notice: Subject to any disclaimer, the term of this patent is extended or adjusted under 35 U.S.C. 154(b) by 0 days.

(21) Appl. No.: 09/214,784
(22) PCT Filed: Jun. 26, 1997
(86) PCT No.: PCT/GB97/01747
  § 371 Date: Jan. 15, 1999
  § 102(e) Date: Jan. 15, 1999
(87) PCT Pub. No.: WO98/02777
  PCT Pub. Date: Jan. 22, 1998

(30) Foreign Application Priority Data

Jul. 12, 1996 (GB) .................................................. 9615830

(51) Int. Cl.[7] ...................................................... H01S 3/10
(52) U.S. Cl. ................................. 372/22; 372/20; 372/31; 372/100; 372/102; 372/92; 359/330
(58) Field of Search .................. 372/22, 20, 92, 372/721, 31, 100, 102; 359/330

(56) References Cited

U.S. PATENT DOCUMENTS 5,033,057 * 7/1991 Bosenberg et al. ..................... 372/21
5,047,668 * 9/1991 Bosenberg ............................ 372/21

(List continued on next page.)

FOREIGN PATENT DOCUMENTS 0 604 303 A   6/1994   (EP) .

OTHER PUBLICATIONS

Patent Abstracts of Japan vol. 096, no. 9, Sep. 30, 1996 & JP 08 128949 A (Ishikawajima Harima Heavy Ind Co Ltd: Ishikawajima Shibuaura Mach Co Ltd), May 21 1996, see abstract.

(List continued on next page.)

Primary Examiner—Leon Scott, Jr.
(74) Attorney, Agent, or Firm—Nixon & Vanderhye P.C.

(57) ABSTRACT

A laser device comprises a non-collinear optical parametric generator (OPG) and a pump wave source (4). The OFG comprises a non-linear crystal (1) fixedly mounted within the generator wherein the relative orientations of the pump wave (3) and each generated wave (5) to an optic axis (2) of the non-linear crystal (1) are substantially such that a point of inflexion is produced in a tuning curve of wavelength versus pump wave orientation of one of the generated waves, such that a broadband spectral output is obtained. This device has many applications including an amplifier for an input seed wave in which the crystal dose not have to be rotated to match the wavelength of the seed wave; or as part of a continuously tuneable narrowband source.

9 Claims, 5 Drawing Sheets

U.S. PATENT DOCUMENTS

| | | | | |
|---|---|---|---|---|
| 5,159,487 | * | 10/1992 | Geiger et al. | 372/21 |
| 5,390,211 | * | 2/1995 | Clark et al. | 372/22 |
| 5,457,707 | * | 10/1995 | Sobey et al. | 372/22 |
| 5,465,147 | | 11/1995 | Swanson . | |
| 5,577,058 | * | 11/1996 | Kafka et al. | 372/20 |
| 5,594,592 | * | 1/1997 | Harlamoff et al. | 372/21 |
| 5,652,757 | * | 7/1997 | Okazaki et al. | 372/22 |
| 5,661,595 | * | 8/1997 | Stamm et al. | 372/22 |
| 5,781,571 | * | 7/1998 | Nabors et al. | 372/21 |
| 5,841,570 | * | 11/1998 | Velsko | 372/21 |
| 6,031,853 | * | 2/2000 | Greene et al. | 372/22 |

OTHER PUBLICATIONS

Wang J et al: Polychromatic optical parametric generation by simultaneous phase matching over a large spectral bandwidth: Optics Letters, Jun. 1 1997, OPT. SOC. AMERICA, USA, vol. 22, no. 11, ISSN 0146–9592 pp. 763–765, XP002043138 see the whole document.

Trapani Di P et al: Efficient Conversion of Femtosecond Blue Pulses by Travelling–Wave Parametric Generation in Non–Collinea Phase Matching: Optics Communications, vol. 119, no. ¾, Sep. 1995, pp. 327–332, XP000518530 see paragraph 2–3.

Agnesi A et al: "beta–Barium borate and lithium triborate picosecond parametric oscillators pumped by a frequency–tripled passive negative–feedback mode–locked Nd: YAG laser" Journal of the Optical Society of America B (Optical Physics), Nov. 1993, USA, vol. 10, no. 11, ISSN 0740–3224, pp. 2211–2217, XP002043139 see abstract; figure 7.

Krylov V et al: "Noncollinear parametric generation in LilO/sub3/ and beta–barium borate by frequency–doubled femtosecond Ti:sapphire laser pulses" Optics Letters, Jan. 15 1995, USA, vol. 20, no. 2, ISSN 0146–9592, pp. 151–153, XP002043140 see p. 153.

* cited by examiner

LASER DEVICE

BACKGROUND OF THE INVENTION

1. Field of the Invention

This invention relates to a laser device.

2. Discussion of Prior Art

Optical parametric generator's (OPG's) have been used to generate laser-like output within a certain spectral range. The OPG comprises a non-linear crystal material to which a pump source is applied. The spectral range is constrained by the pump source wavelength, the type of non-linear material used and the relevant geometry-type implemented. The output of an OPG is usually of relatively narrow spectral bandwidth, centred at a wavelength determined by the angle of the crystal axis relative to the pump to axis. Conventionally, the centre wavelength can be continuously tuned by altering the orientation or changing the temperature of the crystal, tuning taking place through consideration of the principle of conservation of momentum, namely phase matching in the terminology of non-linear optics. Normally, for a certain orientation of the crystal, only a narrow spectral range of signal and idler wavelengths satisfy the phasematch constraints, thus only a narrow spectral range of signal and idler wavelengths can be generated simultaneously. Attempts have been made to obtain broader spectral bandwidth output using dye or vibronic laser systems, but the dyes used in dye systems may be harmful and special safety precautions are required, while vibronic systems are complex to operate and the bandwidths obtained are small, typically less than 50 nm.

SUMMARY OF THE INVENTION

In accordance with a first aspect of the present invention, a laser device comprises a non-collinear optical parametric generator (OPG); and a pump wave source; the OPG comprising a non-linear crystal fixedly mounted within the generator; wherein the relative orientations of the pump wave and each generated wave to an optic axis of the non-linear crystal are substantially such that a point of inflexion is produced in a tuning curve of wavelength versus pump wave orientation of one of the generated waves, whereby a broadband spectral output is obtained.

The present invention produces a broadband output from a device which is robust and safer and simpler to use than conventional broadband devices, as well as giving a greater bandwidth.

Preferably, the device further comprises reflecting means for forming a resonator in which at least one of the generated waves is resonant. The pump wave may enter the OPG directly or through the reflecting means, but preferably, the laser device further comprises a pair of reflectors, whereby the pump wave is coupled to the OPG.

Preferably, the reflectors comprise a pair of dichroic mirrors.

Preferably, the device further comprises pump wave reflecting means, whereby the intensity of the pump wave source is enhanced.

In accordance with a second aspect of the present invention, an amplifier comprises a device according to the first aspect and means for injecting a seed wave into the device.

In a conventional narrowband OPG amplifier, the crystal within the OPG has to be rotated to match the wavelength of the seed wave, but in the present invention this is not required, leading to a simpler construction. The invention also enables a broader gain bandwidth and enhanced spectral coverage to be achieved for broadband amplification.

In accordance with a third aspect of the present invention, a continuously tuneable narrowband source comprising a laser device according to the first aspect of the invention, further comprises reflecting means; wherein the reflecting means comprise at least one mirror and tuning means; and wherein the at least one mirror is fixed and the tuning means are movably mounted, such that a continuously tuneable narrowband output is produced.

Conventionally, the crystal would need to be reoriented each time the source is tuned, whereas the present invention only requires the tuning means to be adjusted.

The tuning means may comprise an etalon, but preferably, the tuning means are dispersive. Any suitable component which has dispersive properties may be used, but preferably, the dispersive tuning means comprise a Littrow or Littman mounted grating, a Littrow prism or an acousto-optic deflector.

In accordance with a fourth aspect of the present invention, a coherence tomography source comprises a laser device according to the first aspect of the invention.

The increased bandwidth of the device of the present invention, gives a shorter coherence length permitting 3-D imaging with enhanced resolution.

In accordance with a fifth aspect of the invention, a system for spectral analysis of a medium comprises a laser device according to the first aspect of the invention; the system further comprising analysing means; wherein one of the generated waves comes into contact with a medium; and the analysing means analyse the spectrum of the generated wave after contact.

BRIEF DESCRIPTION OF THE DRAWINGS

Examples of a laser device in accordance with the present invention and applications thereof will now be described with reference to the accompanying drawings in which.

DETAILED DISCUSSION OF PREFERRED EMBODIMENTS

Figure 1:
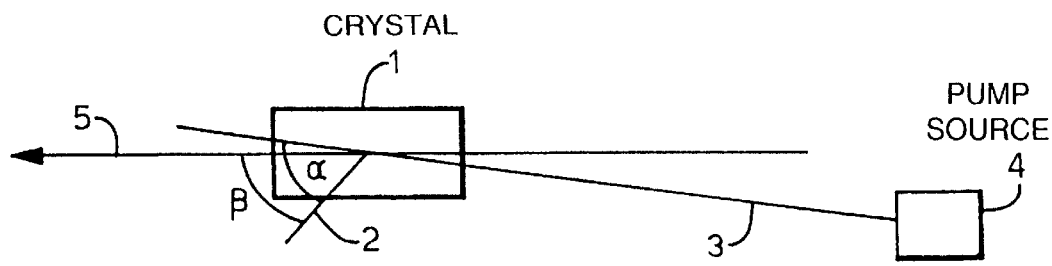
FIG. 1 shows a laser device according to the present invention.
Figure 2:
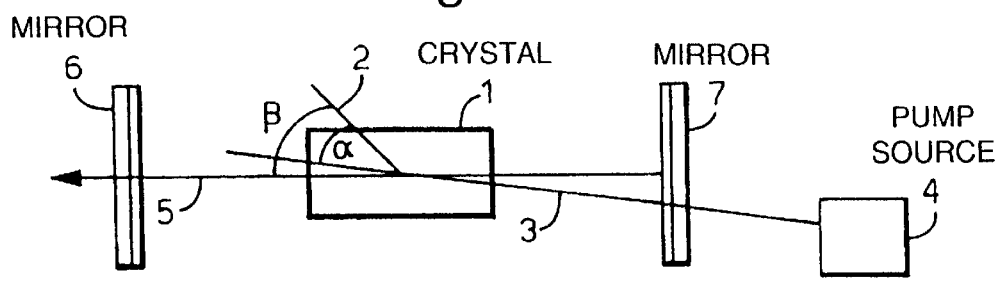
FIG. 2 shows a laser device according to the present invention adapted to form an oscillator.

FIG. 1 illustrates a first example of a laser device according to the invention. The device comprises an optical parametric generator (OPG) formed of a non-linear crystal 1 in which an optic axis 2 is defined. A pump wave 3 is input from a pump source 4 and exits from the crystal 1 at an angle a to the optic axis 2. A generated wave 5 exits the crystal at an angle β to the optic axis 2. In FIG. 2 a pair of mirrors 6,7 are provided which define a standing wave resonator for the generated signal wave 5, the resonant wave in this case, so forming an optical parametric oscillator (OPO). Alternatively, with an additional mirror, the mirrors 6,7 could form a ring cavity.

Figure 3:
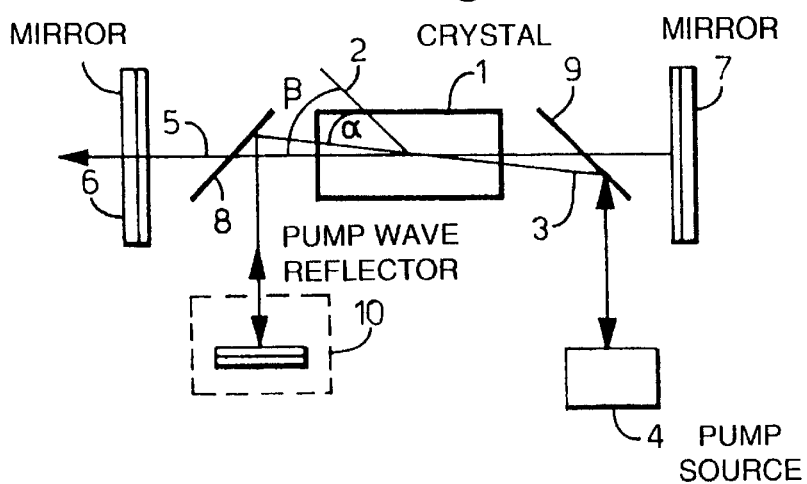
FIG. 3 shows a laser device according to the present invention with additional pump wave coupling reflectors.

The pump wave 3 may enter either through or around the mirrors 6,7 or, as illustrated in FIG. 3, via a pair of reflectors 8,9 which couple the pump wave 3 from the pump source 4 into the crystal 1. Typically, these reflectors are dichroic mirrors, so that only the pump wave is reflected and the signal wave passes through them. An optional feature shown in FIG. 3 is a pump wave reflector 10 which increases the intensity of the pump source 4 by double passing the pump wave 3.

The pump wave 3 is incident on the crystal 1 and an output signal wave 5 and idler wave (not shown) are generated. In these examples, the crystal 1 is of beta barium borate (BBO), which is readily available, and the OPG has a type I non-collinear phasematch geometry. Other types of crystal can be used, including lithium triborate (LBO) and periodically poled non-linear materials, such as periodically poled lithium niobate (PIPLN). By varying the periodic polling, quasi-phase matching is created allowing higher non-linear coefficients to be exploited. The type I geometry is so defined that the polarisation direction of the pump wave 3 is orthogonal to the polarisation direction of both the signal wave 5 and the idler wave. The non-linear crystal 1 is so arranged that the resonated signal wave 5 and pump wave 3 pass through the crystal 1 at a specific set of angles α,β of pump wavevector direction and signal wavevector direction respectively relative to the optic axis 2.

Figure 4:
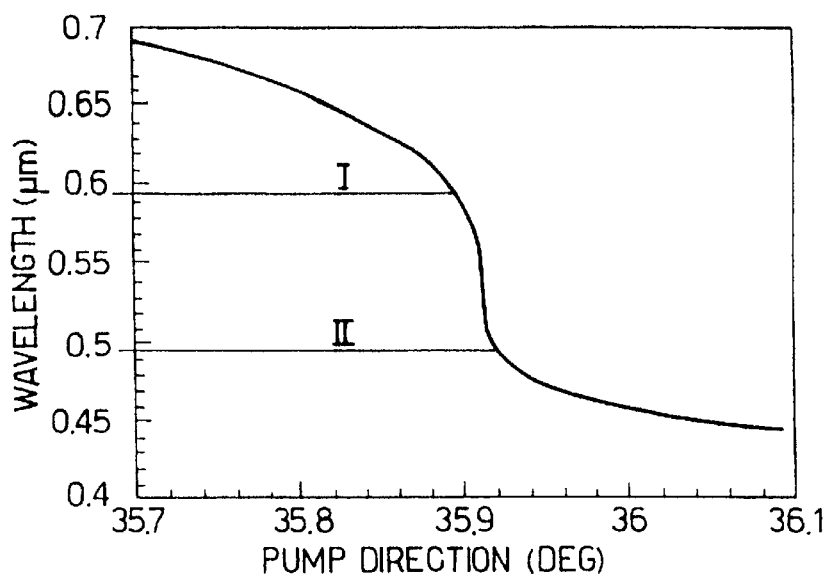
FIG. 4 shows a tuning curve for the device of FIG. 3.

In operation, the OPO is pumped by the third harmonic (355 nm) of a Q switched neodymium yttrium aluminium garnate (Nd:YAG) laser. Pump pulse energies were up to 15 mJ in a duration of 10 nsec. In the particular configuration of FIG. 3 the angles were signal wavevector direction β=40.3° relative to the optic axis 2 and pump wavevector direction α=35.9° relative to the optic axis. The angles given are approximate, the condition being that they are the approximate angles for signal wavevector direction and pump wavevector direction at which a point of in flexion occurs in a curve of wavelength against pump wave orientation. In this geometry walk off is partially compensated for by the non-collinearity. However, it is not essential to compensate for walkoff. The BBO crystal was cut at θ=40° and has dimensions 8×4×18 mm³. Input and exit faces were broadband anti-reflection coated with a single layer magnesium fluoride coating. For this crystal and pump geometry, noting the inherent divergence of the pump beam of 0.6 mrad, the usual phasematch condition of $\Delta k < \pi/1$ predicts that for a crystal length (1) of 18 mm, broadband oscillation should be observed over the range 500 nm to 600 nm, as shown in FIG. 4, which illustrates the tuning curve of this geometry. It is to be noted that as there is little walk-off effect in this configuration, a long crystal can be used. A similar spectral range to this has been observed experimentally.

Figure 5:
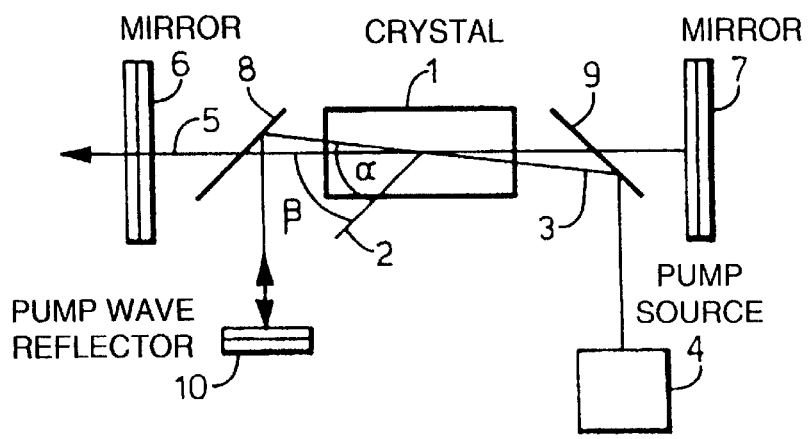
FIG. 5 is a further laser device according to the present invention.
Figure 6:
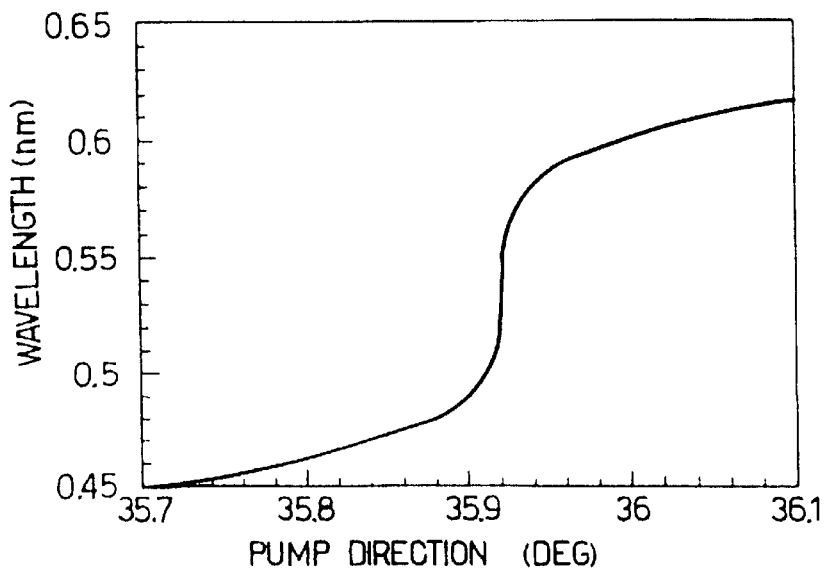
FIG. 6 shows a tuning curve for the device of FIG. 5.

FIG. 5 shows a further example with the signal wavevector direction arranged at β=31.5° relative to the optic axis 2 and with the pump wavevector angle, α=35.9°. Although this configuration has a relatively large walk-off angle compared to the first example, it has a larger acceptance angle and effective non-linear coefficient. Its bandwidth of output is similar to that of the FIG. 3 example as illustrated by the tuning curve in FIG. 6.

Figure 7:
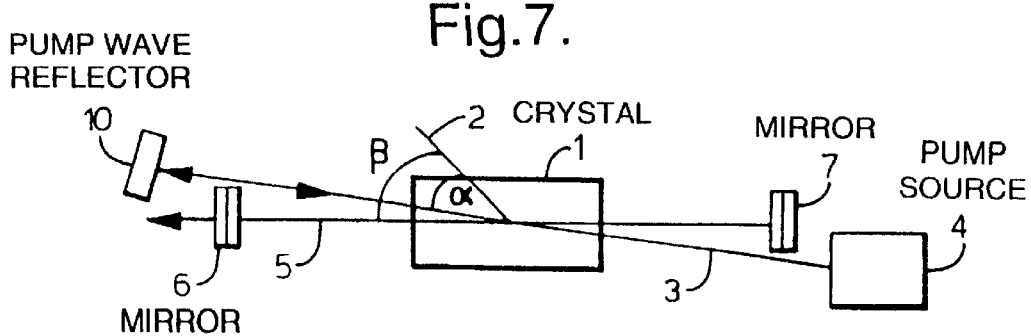
FIG. 7 is a laser device according to the invention having a type II phase matching geometry.
Figure 8:
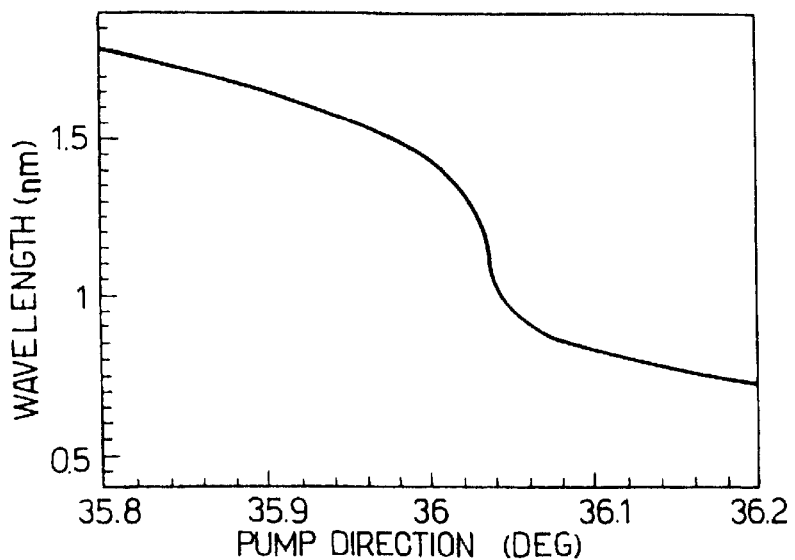
FIG. 8 is a tuning curve for the device of FIG. 7.

Another example is shown in FIG. 7. This shows a type II non-collinear OPO utilising BBO as the non-linear crystal material. The type II geometry is so defined that the polarisation vectors of the signal and idler waves are orthogonal to each other, while one is parallel to the polarisation vector of the pump wave. The particular configuration for this OPO is the signal wavevector direction β=40.5° relative to the optic axis 2; pump wavevector direction, α=36.05° relative to the optic axis. The significance of this configuration is its potential for demonstrating an extremely broad bandwidth, ranging from about 900 nm to 1300 nm as shown in FIG. 8.

Figure 9:
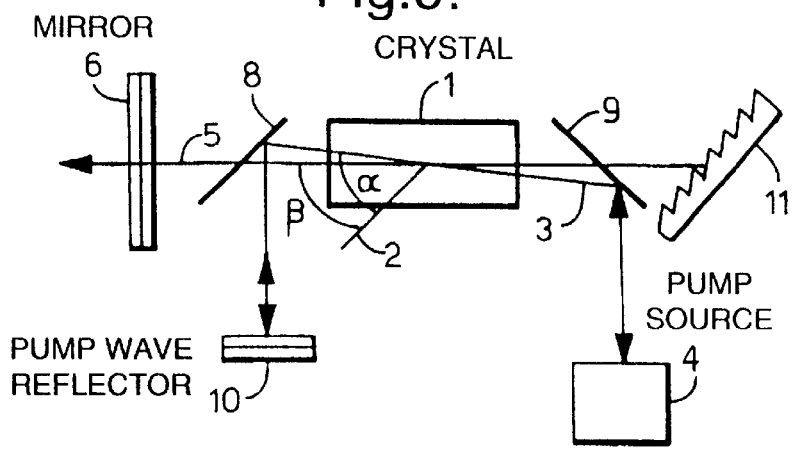
FIG. 9 is a laser device according to the invention for producing a tuned narrowband output.

In the example of FIG. 9, a continuously tuneable narrowband source is illustrated. This makes use of a laser device similar to those described in the previous embodiments, except that one of the OPO resonator mirrors 7 has been replaced with a dispersive element, in this example either a Littrow or Littman mounted grating 11. The advantage of this arrangement is that there is no need to alter the orientation of the non-linear crystal 1, which can be a significant problem in conventional narrowband sources. FIG. 9 demonstrates this embodiment for a first order Littrow mounted grating. In a conventional narrowband source, it is necessary to make complementary adjustments to both the non-linear crystal orientation and the grating orientation to effect tuning of such a narrowband device. Implementing a suitable phasematching geometry in the laser device of the present invention alleviates this complexity, by removing the requirement to adjust the crystal orientation while retaining the adjustment of the grating 11 as a means of controlling the wavelength of the spectral output.

Figure 10:
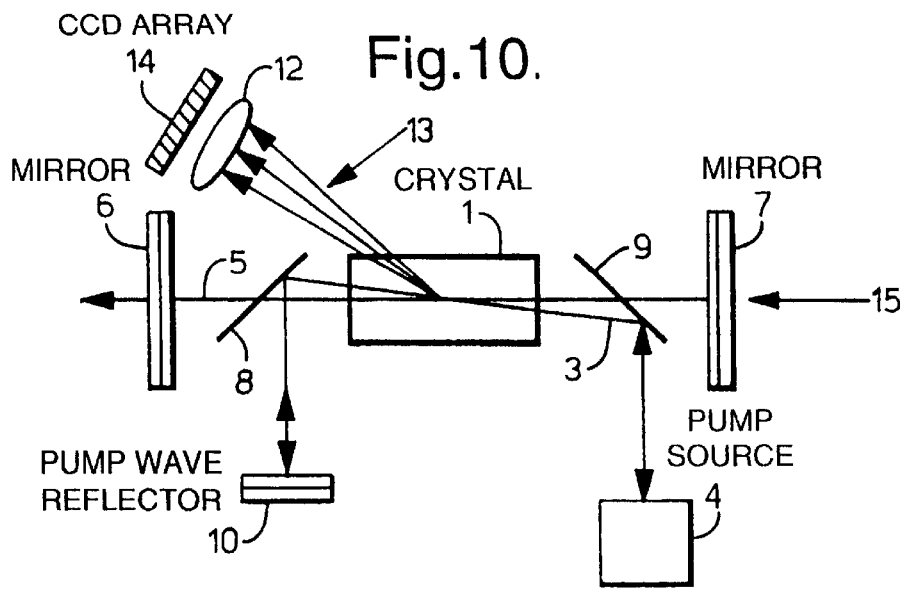
FIG. 10 shows a system for spectral analysis incorporating a laser device according to the invention.
Figure 11:
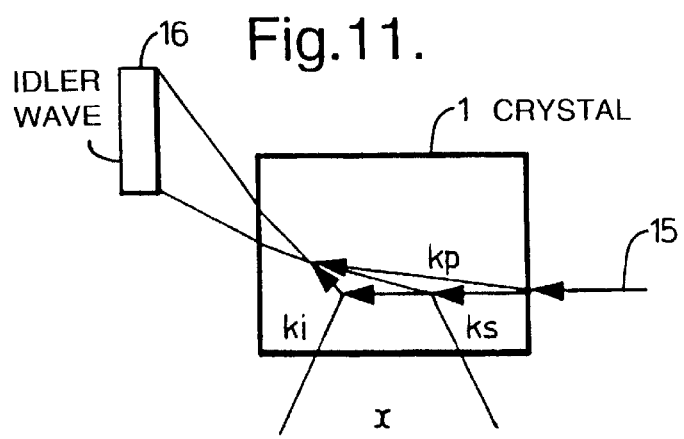
FIG. 11 illustrates wave generation in the system of FIG. 10.

Another application of the laser device is in operation as a spectral analyser utilising the spatially dispersed characteristics of one of the generated waves. The nature of operation of the device requires that for every photon of light generated at one of the generated wave frequencies, either signal or idler wave, there is a second photon generated at one of the complementary wave frequencies, where conservation of energy requires that $\omega_p = \omega_s + \omega_i$ where p, s and i refer to the pump wave and two generated waves, signal and idler. If preferential or enhanced operation of the device is established at some signal wave frequency, then preferential or enhanced output is also observed at some corresponding idler frequency. By imaging the spatially dispersed idler wave 13 via a lens 12 onto, for example, a CCD array 14 any fluctuation in the intensity of the dispersed wave can be measured. This effect can be exploited in performing spectral analysis in for example the following different ways:

(i) If light 15 of a frequency within the spectral range of the signal wave generated in a laser device similar to the type described in the first four embodiments, is injected into the nonlinear crystal 1, then preferential gain will be observed at that frequency with a corresponding enhancement in the intensity of the secondary wave monitored on the CCD array 14. With appropriate numerical analysis the presence, wavelength and intensity of the injected wave can then be deduced, so acting as a broadband light detector and spectral analyser. This is illustrated schematically in FIGS. 10 and 11. FIG. 11 shows the non-collinear phasematching mechanism depicting generation of the coaxial and spatially dispersed waves where x is the analysable bandwidth and a spatially dispersed idler wave 16 is generated from the injected light 15 which has passed through the crystal 1. The device in this arrangement can be used in remote pollution monitoring, for example to identify and monitor $CO_2$ levels or other harmful gases in the atmosphere, or the presence of pollutants such as oil, sewage or chemical spills in rivers and estuaries.

Figure 12:
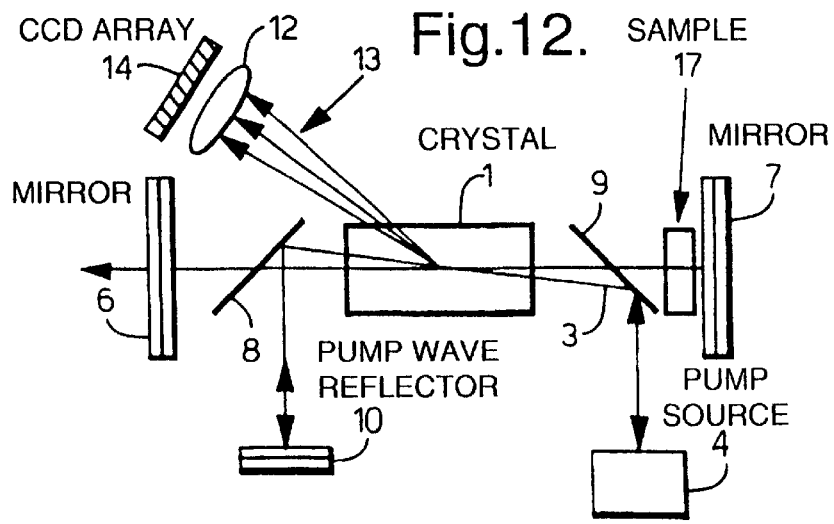
FIG. 12 shows another system for spectral analysis incorporating a laser device according to the invention.

(ii) The absorption characteristics of materials may be studied in device types similar to that shown schematically in FIG. 12. An absorbing sample could be positioned outside the OPO, but in this case the sample 17 is located within the OPO. The sample absorbs light at frequencies within the signal wave spectral range of the OPO. Consequently these frequencies are suppressed and again this modulation appears in the profile of the complementary dispersed wave monitored on the CCD array 14. The applications of this example are the same as for FIG. 10, but for the case where it is possible to collect a sample, rather than remote operation. As an alternative spectral analysis application, the laser device may be used as a source of broadband light for differential absorption light detecting and ranging (DIAL).

Figure 13:
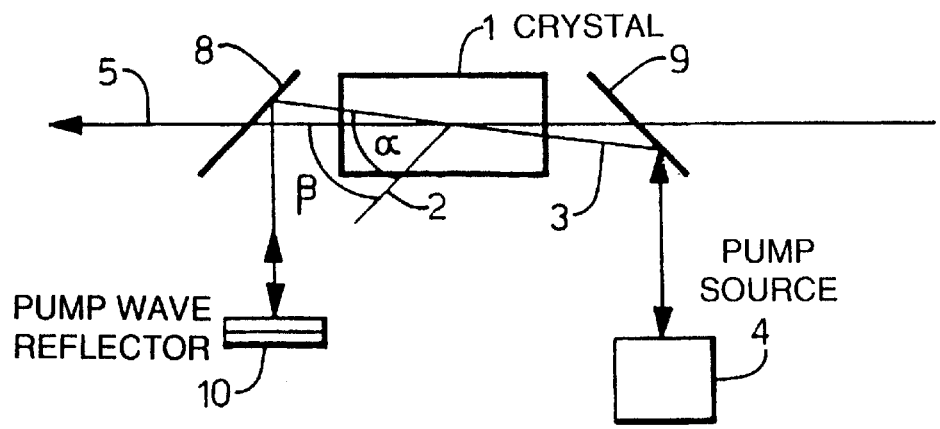
FIG. 13 illustrates a broadband optical parametric amplifier (OPA) geometry incorporating a laser device according to the invention; and, FIG. 14 shows a laser device of the present invention in use in an imaging system for high resolution 3D imaging through scattering media.

FIG. 13 illustrates a type I optical parametric amplifier (OPA) utilising BBO as the non-linear medium. The amplifier comprises a noninear crystal 1 having an optic axis 2 and a pair of reflectors 8,9, as well as an optional pump reflector 10. A pump wave 3 is generated by a pump source 4 and a signal wave 5 is seeded by illuminating the non-linear crystal 1 with either broadband or narrowband radiation along the signal wave direction, whereupon those spectral components lying within the phasematchable spectral range defined by the phasematching constraints experience optical gain.

Another application of the device is as an ultrashort pulse generator. The pump source is chosen to have an ultrashort pulse duration and the device is used specifically for generating ultrashort pulses. Minimum pulse duration's achievable are determined by the spectral width of a pulse through the uncertainty relationship $\Delta\upsilon\Delta\tau<1$. The laser device of the present invention broadens the allowable bandwidth of an OPO and consequently permits the generation of shorter duration pulses. Pulse compression is achieved through chirp reversal and self compression in the non-linear crystal.

Figure 14:
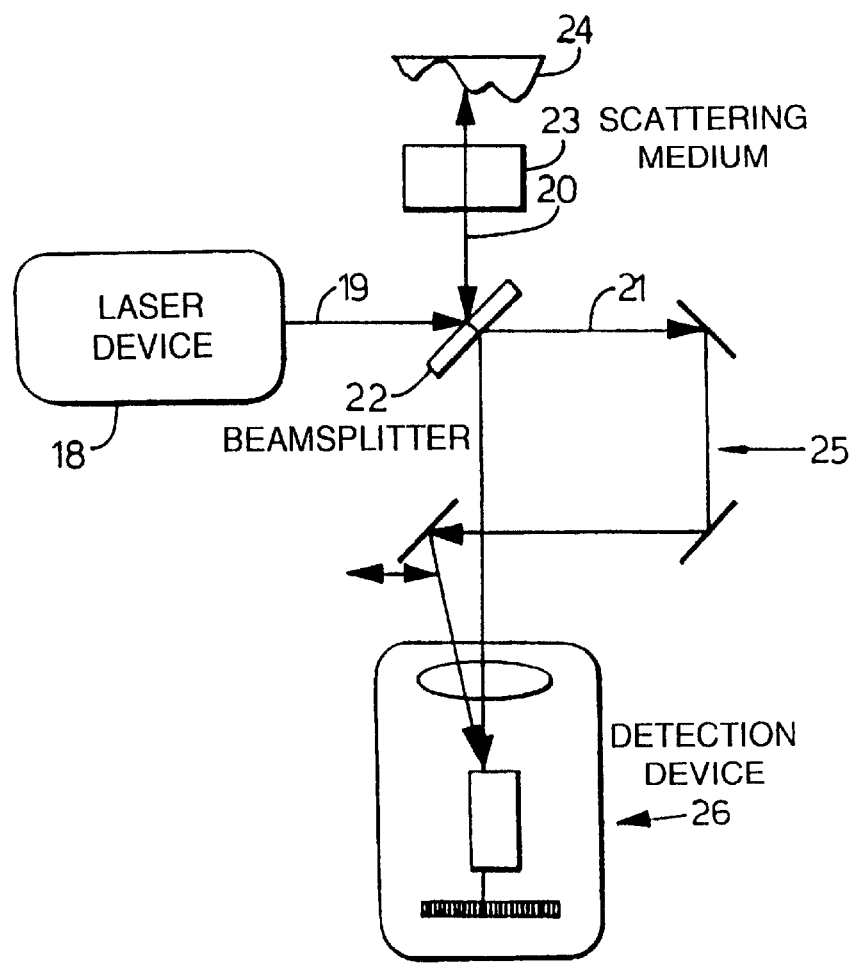

Another application, shown in FIG. 14, for which the device is suitable is as a source 24 for coherence tomography which combines high-depth with high-spatial resolution for imaging applications based on the short coherence length and low beam divergence associated with the polychromatic source. Conventional sources lack the power and bandwidth required to compensate for the scattering effect encountered in turbid media, such as tissue. The laser device 18 may be of the type described herein, and is accompanied by ancillary apparatus in which a collinear, coaxial, polychromatic beam 19 output from the device 18 is split into two beams 20,21 by a beamsplitter 22. One beam 20 traverses a scattering medium 23, in which depth and spatial resolution of an embedded or more distant object 24 is required, so as to strike the object and be backscattered. The other beam 21 traverses an adjustable delay line 25 and the two beams then enter a non-linear coherent detection device 26. Thus an image of the object, e.g. bone or tumour, can be derived for which the effect of the scattering material has been compensated, giving improved images.

The above embodiments are described by way of example only and modifications to them may be made without departing from the scope of the invention. For example, other non-linear materials could be implemented. A feasible configuration of this kind is a type I non-collinear OPG utilising LBO as the non-linear medium, where the signal wavevector direction is 51° relative to the optic axis in the x-y plane; pump wavevector direction is 47.5° relative to the optic axis also in the x-y plane. Further, the centre wavelength of the broadband output can be shifted by using other pumping sources with different lasing wavelengths, such as the output from an Xenon Chloride (XECl) excimer laser operating at 308 nm. In this case the signal wavevector direction for a BBO based device is 47.6° relative to the optic axis and the pump wavevector is 42.5° relative to the optic axis.

What is claimed is:

1. A laser device, the device comprising:
   a non-collinear optical parametric generator (OPG);
   a pump wave source for generating at least one wave as an input to said OPG, the OPG comprising a non-linear crystal fixedly mounted within the generator; and
   reflecting means, coupled to said OPG, for forming a resonator in which said at least one wave is resonant; wherein the pump wave and each generated wave and an optic axis of the non-linear crystal are adapted to produce a point of in flexion in a graph of a tuning curve of wavelength versus pump wave orientation of said at least one generated wave, such that a polychromatic broadband spectral output is obtained.

2. A device according to claim 1, further comprising a pair of reflectors located at an input and an output, respectively, of said crystal coupling said at least one wave from said pump source to the OPG.

3. A device according to claim 2, wherein the reflectors comprise a pair of dichroic mirrors.

4. A device according to claim 1, further comprising a pump wave reflector for reflecting the at least one wave output from said crystal back through said crystal, whereby the intensity of the pump wave source is enhanced.

5. A continuously tuneable narrowband source, the source comprising a device according to claim 1, the device further comprising reflecting means; wherein the reflecting means comprise at least one mirror and tuning means; and wherein the at least one mirror is fixed and the tuning means are movably mounted, such that a continuously tuneable narrowband output is produced.

6. A continuously tuneable narrowband source according to claim 5, wherein the tuning means is dispersive.

7. A source according to claim 6, wherein the dispersive tuning means comprise one of a Littrow mounted grating, a Littman mounted grating, a Littrow prism, and an acousto-optic deflector.

8. A laser device according to claim 1, wherein said device is adapted to provide a coherent beam for coherence tomography.

9. A system for spectral analysis of a medium, the system comprising a laser device according to claim 1, wherein said at least one generated wave comes into contact with a medium, said system further comprising analysing means for analysing the spectrum of the at least one generated wave after contact with the medium.

* * * * *